United States Patent [19]
de Villiers et al.

[11] Patent Number: 6,127,164
[45] Date of Patent: Oct. 3, 2000

[54] HUMAN PAPILLOMA VIRUS TYPE 57, DIAGNOSIS OF HPV 57 INFECTIONS AND METHOD THEREFOR

[75] Inventors: Ethel-Michele de Villiers, Hirschberg; Anja Hirsch-Behnam; Harald zur Hausen, both of Heidelberg, all of Germany

[73] Assignee: Dade Behring Marburg GmbH, Marburg, Germany

[21] Appl. No.: 08/488,359

[22] Filed: Jun. 7, 1995

Related U.S. Application Data

[62] Division of application No. 08/394,215, Feb. 24, 1995, abandoned, which is a continuation of application No. 08/195,064, Feb. 14, 1994, abandoned, which is a continuation of application No. 07/964,308, Oct. 21, 1992, abandoned, which is a division of application No. 07/389,807, Aug. 4, 1989, Pat. No. 5,187,090.

[30] Foreign Application Priority Data

Aug. 6, 1988 [DE] Germany ............................. 38 26 793

[51] Int. Cl.$^7$ .................................................. C12N 7/00
[52] U.S. Cl. .................. 435/235.1; 435/5; 435/287.2; 536/23.72; 424/204.1
[58] Field of Search ................... 435/5, 6, 235.1, 435/172.3; 536/23.72

[56] References Cited

PUBLICATIONS

Fuchs and Pfister, "Cloning and Characterization of Papillomavirus Type 2c DNA", Intervirology 22:177–180 (1984).
Boshart and zur Hausen, "Human Papillomaviruses in Buschke–Löwenstein Tumors: Physical State of the DNA and Identification of a Tandem Duplication in the Noncoding Region of a Human Papillomavirus 6 Subtype", J. of Virology 58(3):963–966 (Jun. 1986).
Murphy & Ward, "Sequencing of Double–Stranded DNA," in Nucleic Acids Sequencing, A Practical Approach, Chapter 4, pp. 99–115 (Howe & Ward eds. 1989).
Sanger et al., "DNA Sequencing With Chain–Terminating Inhibitors, " Proc. Natl. Acad, Sci. USA, vol. 74, No. 12, pp. 5463–5467 (Dec. 1977).
Delius & Hoffmann, "Primer–Directed Sequencing of Human Papillomavirus Types," Current Topics in Microbiology and Immunology, vol. 186, pp. 14–31 (1994).
Coggin, J., Jr. & Zur Hausen, "Workshop on Papillomaviruses and Cancer," Cancer Research, vol. 39, pp. 545–546 (1979).
L. Banks et al., "Expression of Human Papillomavirus Type 6 and Type 16 Capsid Proteins in Bacteria and Their Antigenic Characterization", J. Gen. Virol., vol. 68, pp. 3081–3089 (1987).
L. Gissman et al., Int. J. Cancer, 29:143–146 (1982).
C. Yanisch–Perron et al., Gene, 33:103–119 (1985).
T. Maniatis et al., Molecular Cloning: A Laboratory Manual; Cold Spring Harbor Laboratory Press, New York (1982), Table of Contents.
J. Messing et al., Proc. Nation. Acad. Sci. USA 74:3642–3646 (1977).
H.C. Birnboim and J. Doly, Nucl. Acids Res. 7:1513–1523 (1979).
E.M. Southern, J. Mol. Biol. 98:503–517 (1975).
S.T. Cole and O. Danos, J. Mol. Biol. 193:599–608 (1987).
DeVilliers, E–M, et al., Virology, 171:248–253 (1989).
Shah, K., Virology, ed. B.N. Fields, et al., p. 371–391 (1985).
Kremsdorf, D. et al., J. Virol., 48:340–351 (1983).
Kremsdorf, D. et al., J. Virol., 52:1013–1018 (1984).
Dürst, M. et al., J. Gen. Virol. 66:1515–1522 (1985).
De Villiers, J. Virology, 63:4898–4903 (1989).
Ellis, R.W. et al., In Vaccines Plotkin & Mortimer Eds., W.B. Saunders Co. pp. 568–575 (1988).
Roggenbuck, B. et al., J. Virol. (1991).
Bernard, H.V. et al., EMBOJ. 6(1):133–138 (1987).
Matlashewski, G. et al., J. Gen. Virol., 67:1909–1916 (1986).
Zhou, J. et al., Virology, 181:203–210 (1991).
Zhou, J. et al., Virology, 185:251–257 (1991).
Cole, S.T. et al., J. Mol. Biol., 193:599–608 (1987).
Ghim, S. et al., Virology, 190:548–552 (1992).
Bowie, J. et al., Science, 247:1306–1310 (1990).
Kumar, V. et al., Proc. Natl. Acad. Sci., 87:1337–1341 (1990).
Boslego, J.W. et al., In: Vaccines & Immunotherapy, pp. 211–223 (1991).
Kamtekar, S. et al., Science, 262:1680–1685.
Hirsch—Behnam, A. et al., Virus Research, 18(1):81–98 (1990).

*Primary Examiner*—Laurie Scheiner
*Attorney, Agent, or Firm*—Finnegan, Henderson, Farabow, Garrett & Dunner, L.L.P.

[57] ABSTRACT

The invention describes the isolation for the first time of human papilloma virus (HPV) 57, the partial characterization of its genome and its cloning in pUC 19. This opens up a way of diagnosing those tumors (oral, genital and cutaneous tumors) which are associated with HPV 57.

29 Claims, 2 Drawing Sheets

HUMAN PAPILLOMA VIRUS TYPE 57, DIAGNOSIS OF HPV 57 INFECTIONS AND METHOD THEREFOR

This is a divisional of application Ser. No. 08/394,215, filed Feb. 24, 1995, now abandoned, which is a continuation of application Ser. No. 08/195,064, filed Feb. 14, 1994, now abandoned which is a continuation of application Ser. No. 07/964,308, filed Oct. 21, 1992, now abandoned which is a divisional of application Ser. No. 07/389,807, filed Aug. 4, 1989, now U.S. Pat. No. 5,187,090.

The human papilloma viruses (HPV) form a group of more than 50 different types. HPV has been found associated with benign (warts, condylomas in the genital region) and malignant (carcinomas of the skin and the vagina) epithelial neoplasms. Paplloma viruses cannot be grown in culture. Thus, methods of genetic manipulation are required for the use of human papilloma virus type 57 DNA (HPV 57 DNA) as a diagnostic aid and for obtaining the expression products, for using them as antigens, for isolating antibodies and for preparing corresponding diagnostic aids and therapeutic agents.

The invention is based on the isolation for the first time of HPV 57, partial characterization of its genome and cloning in pUC 19. This opens up a way of diagnosing tumors (oral, genital and cutaneous tumors) associated with HPV 57.

The invention is defined in the patent claims. Further embodiments of the invention are described in detail hereinafter.

The cloning of HPV 57 made it possible to compare with 56 other HPVs. HPV 2 and HPV 27 are very closely related, and hybridization in liquid phase revealed 17% and 25% homology, respectively. The colinearity of HPV 57 with HPV 68 was determined (FIG. 1) and a physical genome nap for restriction enzyme clearages (FIG. 2) was constructed.

This has opened up a way of testing neoplasms (genital and cutaneous tumors), especially tumors on the head, for the presence of HPV 57 and, whore appropriate, a therapeutic approach via antibodies to HPV 57 proteins.

EXAMPLES

1. Isolation of episom HPV 57 DNA

High molecular weight DNA was isolated from an inverted papilloma of the maxillary sinus as described (Gissmann et al. (1982), int. J. Cancer 29, 143–146).

2. Cloning of HPV 57 in the plasmid pUC 19

The known plasmid pUC 19 (Yanish-Perron et al. (1985), Gene 33, 113–119) was chosen as cloning vector. HPV 57-containing cellular double-stranded DNA was cleaved with Eco RI and then cloned into pUC 19 (Xaniatis et al. (1982) Nolecular Cloning: A Laboratory Manual; Cold Spring Harbor Laboratory Press, New York). Recombinant clones were identified in the β-galactosidase test (Messing et al. (1977). Proc. Nat. Acad. Sci. USA 75, 3641–3646) and rapid DNA extraction was followed by analysis of DNA fragments ligated in (Birnboin, H. L. and Doly, J. (1979), Nucl. Acids. Res. 7, 1513–1523).

3. Physical genome maps of HPV 57

HPV 57 DNA detached from the vector by Eco RI cleavage was digested with restriction endonucleases and the corresponding physical genome maps were constructed by generally known methods. The result is summarized in FIG. 2, the sole Eco RI clearage site being used to linearize the HPV 57 molecule. The table shows the length of the individual restriction fragments.

4. Comparison with other HPVs

The DNA of the HPV 57 genome was compared by means of DNA/DNA hybridization under various degrees of stringency with the DNAs of 56 available HPV types (E. M. Southern (1975), J. Mol. Biol. 98, 50–517).

Under high-stringency conditions (melting temperature Tm −20° C.) HPV 57 DNA hybridizes with HPV 2 and HPV 27.

Figure 1:
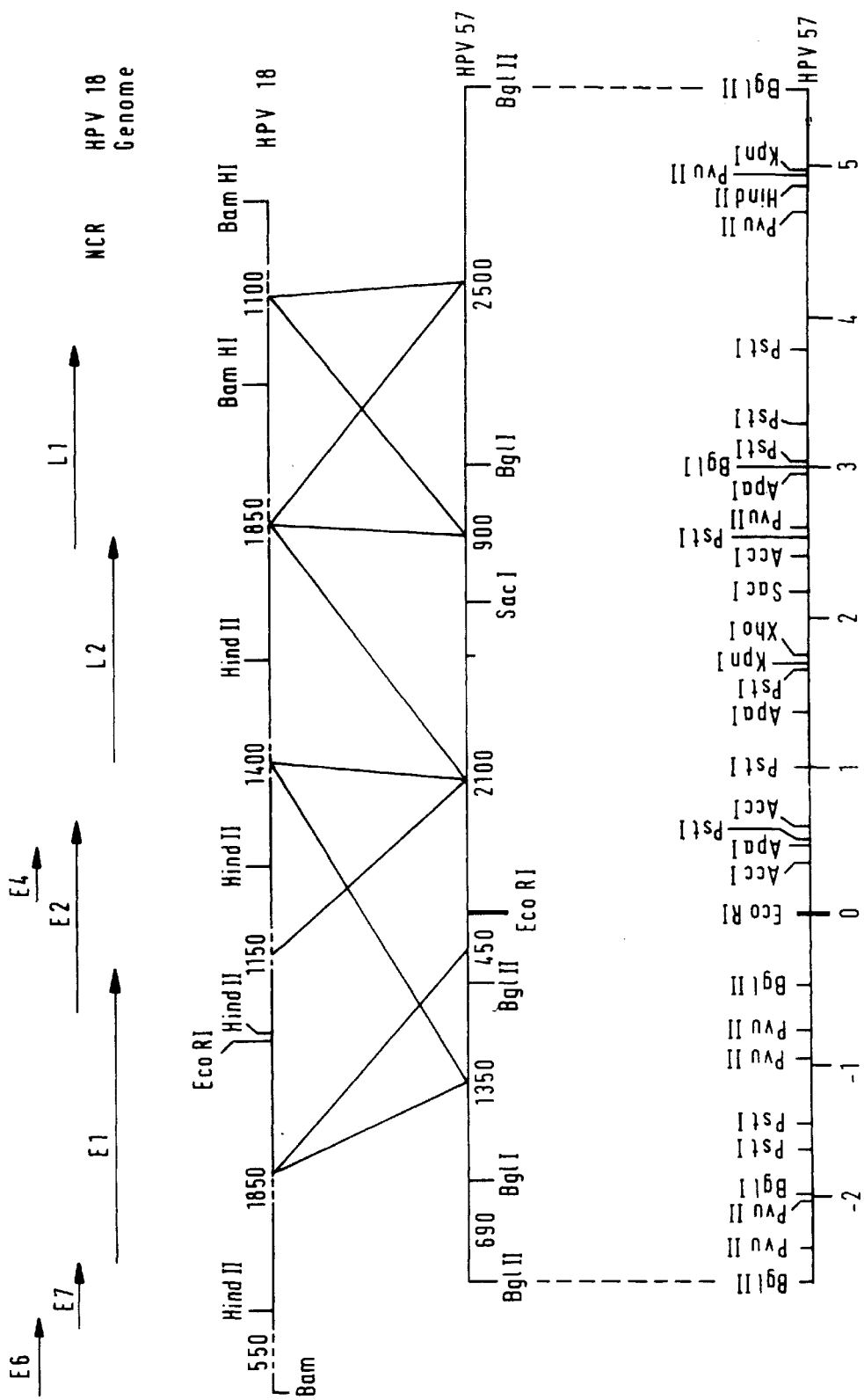
FIG. 1. Colinear alignment of HPV 57 to HPC 18 DNA.

The colinearity with HPV 18 based on hybridization experiments is shown in FIG. 1.

Knowing the HPV 18 DNA sequence (Cole et al. (1987) J. Mol. Biol. 193, 599–608) it is possible to deduce the open reading frames of HPV 57 and thus to obtain the HPV 57 proteins by general methods for subcloning with subsequent expression in prokaryotic or eukaryotic expression systems.

The pUC 19 plassid DNA containing HPV 57 was deposited on Jun. 13, 1988, at the Deutsche Sammlung für Mikroorganismen (German Microorganiss Collection) under the number DSM 4694 in accordance with the Budapest Treaty.

Figure 2:
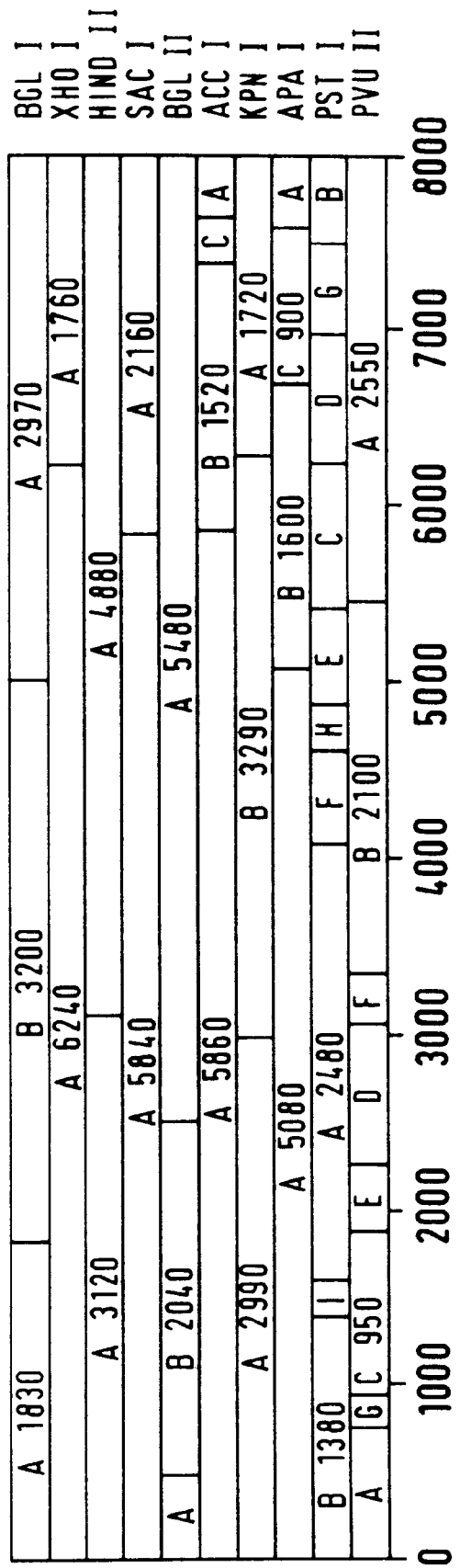
FIG. 2. Restriction enzyme analysis of HPV 57.

Key to FIG. 2

The circular genome was cloned via its Eco RI clearage site, the figures following the letters designating the fragments indicate the length in base-pairs (bp). Restriction enzymes with one cleavage site are KhoI, HindII and SacI. The restriction enzymes ZbaI, SalI, BamHI, HindIII and HpaI do not cleave. The exact location of the four 500 bp-long PstI fragments was not determined.

We claim:

1. A method for the diagnosis of HPV 57 infection comprising using the DNA coding for proteins, or parts of this DNA, wherein said proteins are expression products obtainable by genetic manipulation of isolate HPV 57 DNA, including equivalent variants thereto, coding for HPV 57 proteins, wherein said DNA specifically hybridizes under high stringency conditions to genomic DNA selected from the group consisting of HPV 57 DNA and DNA of HPV 57 equivalent variants, but not to the DNA of other HPV subtypes.

2. A method for the diagnosis of HPV 57 infection as claimed in claim 1 comprising using parts of the DNA coding for HPV 57 proteins.

3. A method for the diagnosis of HPV 57 infection as claimed in claim 1 comprising using equivalent variants of the DNA coding for HPV 57 proteins.

4. A diagnostic aid containing DNA which codes for proteins, or parts of this DNA, wherein said proteins are expression products obtainable by genetic manipulation of isolated HPV 57 DNA, including equivalent variants thereto, coding for HPV 57 proteins, wherein said DNA specifically hybridizes under high stringency conditions to genomic DNA selected from the group consisting of HPV 57 DNA and DNA of HPV 57 equivalent variants, but not to the DNA of other HPV subtypes.

5. A diagnostic aid as claimed in claim 4, comprising parts of the DNA coding for HPV 57 proteins.

6. A diagnostic aid as claimed in claim 4, comprising equivalent variants of the DNA coding for HPV 57 proteins.

7. A method for the diagnosis of HPV 57 infections, which comprises hybridizing the RNA or DNA which is to be examined with DNA which codes for the proteins which are expression products obtainable by genetic manipulation of isolated HPV 57 DNA, including equivalent variants thereto, coding for HPV 57 proteins, or for parts of these proteins, wherein said DNA or RNA specifically hybridizes under high stringency conditions to genomic DNA selected from the group consisting of HPV 57 DNA and DNA of HPV 57 equivalent variants, but not to the DNA of other HPV subtypes.

8. A method for the diagnosis of HPV 57 infection as claimed in claim 7 comprising using parts of the DNA coding for HPV 57 proteins.

9. A method for the diagnosis of HPV 57 infection as claimed in claim 7 comprising using equivalent variants of the DNA coding for HPV 57 proteins.

10. A method for the diagnosis of HPV 57 infections, which comprises hybridizing the DNA which is to be examined with full length HPV 57 DNA.

11. A method for the diagnosis of HPV 57 infections, which comprises hybridizing the DNA which is to be examined with full length DNA of HPV 57 equivalent variants.

12. A method for the diagnosis of HPV 57 infections, which comprises hybridizing the DNA which is to be examined with fragments of HPV 57 DNA as disclosed in FIG. 2.

13. The method for diagnosis of HPV 57 infections of claim 12 wherein the fragments are fragments of DNA of HPV 57 equivalent variants.

14. HPV 57 DNA fragments as disclosed in FIG. 2.

15. The HPV 57 DNA fragments of claim 14, wherein the fragments are fragments of DNA of HPV 57 equivalent variants.

16. A method for the diagnosis of HPV 57 infection comprising hybridizing the DNA which is to be examined with isolated fragments of HPV 57 DNA, wherein said fragments specifically hybridize under high stringency conditions to genomic DNA selected from the group consisting of HPV 57 DNA and DNA of HPV 57 equivalent variants but not to the DNA of other HPV subtypes.

17. A method for the diagnosis of HPV 57 infection comprising hybridizing the DNA which is to be examined with isolated fragments of DNA of HPV 57 equivalent variants wherein said fragments specifically hybridize under high stringency conditions to genomic DNA selected from the group consisting of HPV 57 DNA and DNA of HPV 57 equivalent variants, but not to the DNA of other HPV subtypes.

18. HPV 57 DNA fragments, wherein said fragments specifically hybridize under high stringency conditions to genomic DNA selected from the group consisting of HPV 57 DNA and DNA of HPV 57 equivalent variants, but not to the DNA of other HPV subtypes.

19. DNA fragments of HPV 57 equivalent variants, wherein said fragments specifically hybridize under high stringency conditions to genomic DNA selected from the group consisting of HPV 57 DNA and DNA of HPV 57 equivalent variants, but not to the DNA of other HPV subtypes.

20. A method for the diagnosis of HPV 57 infections, which comprises hybridizing the DNA which is to be examined with fragments of HPV 57 DNA obtained using restriction endonucleases selected from the group consisting of Bgl II, Pvu II, Bgl I, Pst I, EcoRl, Acc I, Apa I, Kpn I, Xho I, Sac I, and Hind II, wherein said fragments specifically hybridize under high stringency conditions to genomic DNA selected from the group consisting of HPV 57 DNA and DNA of HPV 57 equivalent variants, but not to the DNA of other HPV subtypes.

21. The method for diagnosis of HPV 57 infections of claim 20, wherein the DNA fragments are from an HPV 57 equivalent variant.

22. HPV 57 DNA fragments having ends described by the restriction endonuclease map disclosed in FIG. 1, wherein said fragments specifically hybridize under high stringency conditions to genomic DNA selected from the group consisting of HPV 57 DNA and DNA of HPV 57 equivalent variants, but not to the DNA of other HPV subtypes.

23. The DNA fragments of claim 22, wherein the DNA fragments are from an HPV 57 equivalent variant.

24. A method for the diagnosis of HPV 57 infections, which comprises hybridizing the DNA which is to be examined with fragments of HPV 57 DNA having a length of at least 190 nucleotides, wherein said fragments specifically hybridize under high stringency conditions to genomic DNA selected from the group consisting of HPV 57 DNA and DNA of HPV 57 equivalent variants, but not to the DNA of other HPV subtypes.

25. The method for diagnosis of HPV 57 infections of claim 24, wherein the DNA fragments are from an HPV 57 equivalent variant.

26. HPV 57 DNA fragments having a length of at least 190 nucleotides, wherein said fragments specifically hybridize under high stringency conditions to genomic DNA selected from the group consisting of HPV 57 DNA and DNA of HPV 57 equivalent variants, but not to the DNA of other HPV subtypes.

27. The DNA fragments of claim 26, wherein the DNA fragments are from an HPV 57 equivalent variant.

28. A DNA fragment of deposit DSM 4694, wherein said fragment specifically hybridizes under high stringency conditions to genomic DNA selected from the group consisting of HPV 57 DNA and DNA of HPV 57 equivalent variants, but not to the DNA of other HPV subtypes.

29. A method for the diagnosis of HPV 57 infection comprising hybridizing the DNA which is to be examined with one or more of the fragments defined in claim 38.

* * * * *

UNITED STATES PATENT AND TRADEMARK OFFICE
CERTIFICATE OF CORRECTION

PATENT NO. : 6,127,164
DATED : October 3, 2000
INVENTOR(S) : de Villiers et al.

Page 1 of 1

It is certified that error appears in the above-identified patent and that said Letters Patent is hereby corrected as shown below:

<u>Column 3, claim 16,</u>
Line 36, after "variants", insert a comma.

<u>Column 4, claim 20,</u>
Line 8, "EcoRl" should read -- EcoRI --.

<u>Column 4, claim 29,</u>
Line 51, "claim 38" should read -- claim 28 --.

Signed and Sealed this

Eighteenth Day of December, 2001

Attest:

JAMES E. ROGAN
*Attesting Officer*     *Director of the United States Patent and Trademark Office*